United States Patent
Pawlow

(10) Patent No.: US 9,708,429 B2
(45) Date of Patent: Jul. 18, 2017

(54) METHOD OF MAKING IMINOSILANE STABILIZED POLYMERS, POLYMER COMPOSITIONS, AND ARTICLES CONTAINING SUCH POLYMERS

(71) Applicant: Firestone Polymers, LLC, Akron, OH (US)

(72) Inventor: James H. Pawlow, Schwenksville, PA (US)

(73) Assignee: Firestone Polymers, LLC, Akron, OH (US)

( * ) Notice: Subject to any disclaimer, the term of this patent is extended or adjusted under 35 U.S.C. 154(b) by 57 days.

(21) Appl. No.: 14/405,604

(22) PCT Filed: Jun. 5, 2013

(86) PCT No.: PCT/US2013/044245
§ 371 (c)(1),
(2) Date: Dec. 4, 2014

(87) PCT Pub. No.: WO2013/184756
PCT Pub. Date: Dec. 12, 2013

(65) Prior Publication Data
US 2015/0166700 A1   Jun. 18, 2015

Related U.S. Application Data

(60) Provisional application No. 61/656,139, filed on Jun. 6, 2012.

(51) Int. Cl.
| | | |
|---|---|---|
| *C08F 212/08* | (2006.01) | |
| *C07F 7/08* | (2006.01) | |
| *C08F 236/10* | (2006.01) | |
| *C08K 3/36* | (2006.01) | |
| *C08C 2/06* | (2006.01) | |
| *C08C 19/44* | (2006.01) | |
| *B60C 1/00* | (2006.01) | |
| *C08K 3/04* | (2006.01) | |

(52) U.S. Cl.
CPC .......... *C08F 212/08* (2013.01); *B60C 1/0016* (2013.04); *B60C 1/0025* (2013.04); *C07F 7/0854* (2013.01); *C08C 2/06* (2013.01); *C08C 19/44* (2013.01); *C08F 236/10* (2013.01); *C08K 3/04* (2013.01); *C08K 3/36* (2013.01)

(58) Field of Classification Search
CPC ........ C07F 7/0854; C08C 19/22; C08C 19/25
See application file for complete search history.

(56) References Cited

U.S. PATENT DOCUMENTS

| | | |
|---|---|---|
| 6,255,404 B1 | 7/2001 | Hogan et al. |
| 6,369,167 B1 | 4/2002 | Morita et al. |
| 7,342,070 B2 | 3/2008 | Tsukimawashi et al. |
| 7,368,506 B2 * | 5/2008 | Kanenari .................. B60C 1/00 152/510 |
| 2009/0163668 A1 | 6/2009 | Yamada et al. |
| 2009/0292043 A1 | 11/2009 | Kurazumi et al. |
| 2011/0048605 A1 | 3/2011 | Zhang et al. |
| 2011/0146877 A1 | 6/2011 | Tanaka et al. |

FOREIGN PATENT DOCUMENTS

| | | | |
|---|---|---|---|
| JP | 02172992 A | * | 7/1990 |
| JP | 2667420 B2 | | 6/1997 |
| KR | 1020080063181 A | | 7/2008 |

OTHER PUBLICATIONS

Kim, Dong Seok, International Search Report with Written Opinion from PCT/US2013/044245, 10 pp. (Nov. 8, 2013).

* cited by examiner

*Primary Examiner* — Vickey Nerangis
(74) *Attorney, Agent, or Firm* — Meredith E. Hooker; Harry Gwinnell

(57) ABSTRACT

Methods of making polymers by polymerizing conjugated diolefin in a hydrocarbon solvent in the presence of an initiator are described. Trialkyl or triaryl siloxy iminosilane functionalizing agents are reacted with the polymer, followed by desolvatizing the polymer. The resulting polymer not only has good filler interaction and processability, but results in a polymer with stable Mooney viscosity. A polymer made by the process of the present invention, including silica, and carbon black fillers, and rubber compositions, and tires containing side walls and treads containing the polymers are also described.

18 Claims, No Drawings

METHOD OF MAKING IMINOSILANE STABILIZED POLYMERS, POLYMER COMPOSITIONS, AND ARTICLES CONTAINING SUCH POLYMERS

CROSS-REFERENCE TO RELATED APPLICATIONS

The present application may relate to subject matter disclosed in one or more of U.S. patent application Ser. Nos. 14/405,576 entitled "Method of Making Stabilized Polymers, Polymer Compositions, and Articles Containing Such Polymers", 14/405,624 entitled "Method of Making Silanol and Silanediol Stabilized Polymers, Polymer Compostions, and Articles Containing Such Polymers", and 14/405,501 entitled "Method of Making Polymers, Polymer Compositions, and Articles Containing Such Polymers". Each of the aforementioned applications is filed of even date herewith and assigned to an entity common hereto and shares an inventor common hereto. Further, the entirety of each and every one of the aforementioned applications is incorporated herein by reference for all purposes.

TECHNICAL FIELD

The field of art to which this invention pertains is conjugated diolefin polymers, methods of producing the same, and compositions and articles containing such polymers.

BACKGROUND

Many attempts have been made to increase the dispersibility of fillers in polymer compositions. A common method for doing this is to modify the polymer with a functional group that interacts with the filler. Note, for example, U.S. Pat. No. 6,369,167, Patent Application Publication No. 2009/0163668, and U.S. Pat. No. 6,255,404, the disclosures of which are incorporated by reference. Silica fillers, in particular, impart desirable properties to polymers, especially those adapted to tire use. However, the use of silica fillers in polymers can also result in special problems relating to dispersibility and processability. Modifications to polymers to improve silica interaction with the polymer can have adverse effects on the polymer's interaction with carbon black, which also imparts desirable polymer properties to polymers, especially adapted to tire use. Therefore, functional group modification of polymers must produce satisfactory interaction with a variety of fillers. However, this functional group termination may also result in an increase in the Mooney viscosity of the treated polymers (hereinafter the use of Mooney viscosity will refer to conventional Mooney $ML_{1+4/100}$ viscosity measures unless otherwise indicated). Note, for example, U.S. Pat. Nos. 5,659,056; 6,255,404; and 7,342,070, the disclosures of which are incorporated by reference. And Mooney viscosity creep with aging has become even more pronounced with the movement from batch to continuous polymerization. Note also, for example, U.S. Pat. Nos. 3,244,644 and 4,185,042, the disclosures of which are incorporated by reference.

As described above, the polymers are typically terminated using a number of different functional compounds including silane containing compounds to yield silane end-capped polymers. However, upon subsequent desolventization of the alkoxysilane terminated polymers through the use of either steam or heated water, an even larger increase in Mooney viscosity often occurs during the hydrolysis of alkoxysilane end groups thereby leading to coupling of the polymer via formation of Si—O—Si bonds between two end groups. Accordingly, it has been found that many of the processes tried in the past do not actually prevent an increase in Mooney viscosity, but only slow the rate of the hydrolysis reaction and, therefore, the rate of coupling of the polymer. Over a period of time, the slow hydrolysis of the end groups will occur, thereby continuing the problem of increased Mooney viscosity and coupling of the alkoxysilane terminated polymers with aging. Aging of polymers result in issues with rubber consistency, ease of mixing, etc.

Thus, while attempts have been made in the art to improve polymer interaction with various fillers, and improve processability of the polymers, a way to slow down the rate of the hydrolysis reaction and coupling of the alkoxysilane terminated polymers is still needed.

BRIEF SUMMARY OF THE INVENTION

Improved processability of polymers, a way to slow down the rate of the hydrolysis reaction and coupling of siloxane end groups of polymers, along with improved filler interaction, is accomplished with the present invention by polymerizing conjugated diolefins in solvents such as hydrocarbon solvents in the presence of an initiator, followed by reaction of the living polymer with functionalizing agents such as trialkylsiloxy or triarylsiloxy iminosilanes. The polymer may then be desolvatized. The resulting polymer not only has good filler interaction and processability, but has improved Mooney viscosity stability, even over long periods of time, for example, during storage.

Aspects of the invention include desolvatizing by drum drying, direct drying, or steam desolvatizing; the use of iminosilane functionalizing agents such as

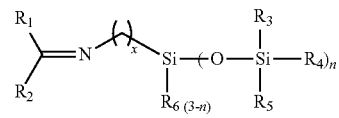

wherein $R_1$ to $R_6$ are $C_1$ to $C_{20}$ alkyl or aryl groups, optionally containing heteroatoms or functional groups, and x being equal to or greater than 1, and n being between 1 and 3; polymer functionalizing agents having the above formula; the use of iminosilane terminal functionalizing agents such as 3-(1-methylethylidene)aminopropyltris(trimethylsiloxy) silane; the use of an initiator such as n-butyl lithium; and the use of hydrocarbon solvents such as one or more hexanes.

Aspects of the invention include the use of a conjugated diolefin such as 1,3-butadiene; the use of an aromatic vinyl compound in the initial polymerizing step; the use of an aromatic vinyl compound such as styrene in the polymerization step; drying the polymer after desolvatizing; the addition of a silica filler to the polymer; and the optional addition of a carbon black filler to the polymer.

Aspects of the invention include the polymers produced by the processes recited above; a conjugated diolefin polymer containing alkylsiloxy or arylsiloxy iminosilane terminal end groups, having a stable Mooney viscosity; rubber compositions containing a filler and the polymer produced by the process described above; and tires containing the rubber of the present invention.

These and other objects, aspects, embodiments and features of the invention will become more fully apparent when read in conjunction with the following detailed description.

DETAILED DESCRIPTION OF THE INVENTION

The particulars shown herein are by way of example and for purposes of illustrative discussion of the various embodiments of the present invention only and are presented in the cause of providing what is believed to be the most useful and readily understood description of the principles and conceptual aspects of the invention. In this regard, no attempt is made to show details of the invention in more detail than is necessary for a fundamental understanding of the invention, the description making apparent to those skilled in the art how the several forms of the invention may be embodied in practice.

The present invention will now be described by reference to more detailed embodiments, with occasional reference to the accompanying drawings. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise. All publications, patent applications, patents, and other references mentioned herein are expressly incorporated by reference in their entirety.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Every numerical range given throughout this specification will include every narrower numerical range that falls within such broader numerical range, as if such narrower numerical ranges were all expressly written herein.

Additional advantages of the invention will be set forth in part in the description which follows, and in part will be obvious from the description, or may be learned by practice of the invention. It is to be understood that both the foregoing general description and the following detailed description are exemplary and explanatory only and are not restrictive of the invention, as claimed.

Attempts to address some of the above issues are described, for example, in U.S. Pat. No. 5,659,056 which describes a process to treat the polymer prior to desolventization with a $C_1$ to $C_{12}$ aliphatic or $C_6$ to $C_{12}$ cycloaliphatic or aromatic carboxylic acid viscosity stabilizing agent soluble in the solvent used to prepare the polymer. U.S. Pat. No. 6,255,404 describes a method for stabilizing the Mooney viscosity of alkoxysilane terminated polymer having at least one hydrolyzable substituent on the silane end group with an alkyl trialkoxysilane viscosity stabilizing agent. U.S. Pat. No. 7,342,070 teaches improving polymer properties by bonding a primary amino group and an alkoxysilyl group to the polymer chain.

Polymers that can be stabilized in accordance with the process of the present invention can be any conjugated diolefins known in the art including polybutadiene, polyisoprene, and the like, and copolymers thereof with monovinyl aromatics such as styrene, alpha methyl styrene and the like, and trienes such as myrcene. Thus, the polymers include diene homopolymers and copolymers thereof with aromatic vinyl compounds. Exemplary diene homopolymers are those prepared from diolefin monomers having from about 4 to about 12 carbon atoms. Exemplary vinyl aromatic polymers are those prepared from monomers having from about 8 to about 20 carbon atoms.

Preferred polymers include diene homopolymers such as polybutadiene and polyisoprene and copolymers such as styrene butadiene rubber (SBR). Polymers and copolymers can comprise from 100 to about 20 percent by weight of diene units and from 0 to about 80 percent by weight of monovinyl aromatic hydrocarbon or triene units, totaling 100 percent. The copolymers may be random copolymers or block copolymers. Block copolymers include, but are not limited to, poly(styrene-butadiene-styrene), which are thermoplastic polymers. The polymers utilized and treated in accordance with the process of the present invention display utility in a number of applications, including, for example, use in the manufacture of tires.

The polymers employed in the practice of this invention can be prepared by employing any polymerization techniques. These techniques include, but are not limited to, cationic and anionic techniques, transition metal or coordination catalyst techniques, emulsion techniques, etc. Similarly, any organic alkali metals and/or the organic alkali earth metals may be used in the polymerization process of the present invention, including alkyllithiums such as n-butyllithium, s-butyllithium and t-butyllithium, alkylenedilithiums such as 1,4-dilithiobutane, phenyllithium, stilbenelithium, lithiumnaphthalene, sodiumnaphthalene, potassiumnaphthalene, n-butylmagnesium, n-hexylmagnesium, ethoxycalcium, calcium stearate, t-butoxystrontium, ethoxybarium, isopropoxybarium, ethylmercaptobarium, t-butoxybarium, phenoxybarium, diethylaminobarium, and barium stearate. Polymerization of the monomers may be conducted in the presence of an organolithium anionic initiator catalyst composition. The organolithium initiator employed may be any anionic organolithium initiators useful in the polymerization of 1,3-diene monomers. In general, the organolithium compounds include hydrocarbon containing lithium compounds of the formula $R(Li)_x$ wherein R represents hydrocarbon groups containing from one to about 20 carbon atoms, and preferably from about 2 to about 8 carbon atoms, and x is an integer from 1 to 2. Although the hydrocarbon group is preferably an aliphatic group, the hydrocarbon group may also be cycloaliphatic or aromatic. The aliphatic groups may be primary, secondary, or tertiary groups although the primary and secondary groups are preferred. Examples of aliphatic hydrocarbyl groups include methyl, ethyl, n-propyl, isopropyl, n-butyl, sec-butyl, t-butyl, n-amyl, sec-amyl, n-hexyl, sec-hexyl, n-heptyl, n-octyl, n-nonyl, n-dodecyl, and octa-decyl. The aliphatic groups may contain some unsaturation such as allyl, 2-butenyl, and the like. Cycloalkyl groups are exemplified by cyclohexyl, methylcyclohexyl, ethylcyclohexyl, cycloheptyl, cyclopentylmethyl, and methylcyclopentylethyl. Examples of aromatic hydrocarbyl groups include phenyl, tolyl, phenylethyl, benzyl, naphthyl, phenyl cyclohexyl, and the like.

Specific examples of organolithium compounds which are useful as anionic initiators in the polymerization of conjugated dienes in accordance with the process of the present invention include, but are not limited to, n-butyl lithium, s-butyl lithium, n-propyl lithium, isobutyl lithium, tertiary butyl lithium, amyl-lithium, and cyclohexyl lithium. Mixtures of different lithium initiator compounds also can be employed preferably containing one or more lithium compounds such as $R(Li)_x$, R and x as defined above. Other lithium catalysts which can be employed alone or in combination with the hydrocarbyl lithium initiators are tributyl tin lithium, lithium dialkyl amines, lithium dialkyl phosphines, lithium alkyl aryl phosphines and lithium diaryl phosphines. The preferred organolithium initiator is n-butyl lithium and in situ produced lithium hexamethylenimide initiator.

The amount of initiator required to effect the desired polymerization can be varied over a wide range depending upon a number of factors such as the desired polymer molecular weight, the desired 1,2- and 1,4-content of the conjugated diene, and the desired physical properties for the polymer produced. In general, the amount of initiator utilized may vary from as little as 0.2 millimole of lithium per 100 grams of monomers up to about 100 millimoles of lithium per 100 grams of monomers, depending upon the desired polymer molecular weight (typically 1,000 to 100,000,000 number average molecular weight).

The polymerizations of the present invention may be conducted in an inert solvent and would consequently be solution polymerizations. The term "inert solvent" means that the solvent does not enter into the structure of the resulting polymer, does not adversely affect the properties of the resulting polymer, and does not adversely affect the activity of the catalyst employed. Suitable inert solvents include hydrocarbon solvents which may be contain aliphatic, aromatic or cycloaliphatic hydrocarbons such as hexane, pentane, toluene, benzene, cyclohexane and the like. Ethers such as tetrahydrofuran and tertiary amines such as triethylamine and tributylamine may also be used as solvents, but these will modify the polymerization as to styrene distribution, vinyl content and rate of reaction. The preferred solvents are aliphatic hydrocarbons and of these solvents, hexane is particularly preferred, including blends and mixtures of hexanes, e.g., linear and branched, including such things as cyclohexane alone or mixed with other forms of hexane.

Polymerization conditions such as temperature, pressure and time are well known in the art for polymerizing the monomers as described with the anionic initiator as described. For example, for illustrative purposes only, the temperature employed in the polymerization is generally not critical and may range from about −60° C. to about 150° C. Preferred polymerization temperatures may range from about 25° C. to about 130° C. for a polymerization time of a few minutes to up to 24 hours or more, and employing pressures generally sufficient to maintain polymerization admixtures substantially in the liquid phase, preferably at or near atmospheric pressure, depending on the temperature and other reaction parameters. Polymerization of any of the above-identified monomers in the presence of an organolithium initiator results in the formation of a "living" polymer. The lithium proceeds to move down the growing chain as polymerization continues. Throughout formation or propagation of the polymer, the polymeric structure may be anionic and living. In other words, a carbon anion is present. A new batch of monomer subsequently added to the reaction can add to the living ends of the existing chains and increase the degree of polymerization. A living polymer, therefore, may include a polymeric segment having an anionic reactive end. Reference to anionically polymerized polymers or anionically polymerized living polymers refers to those polymers prepared by anionic polymerization techniques.

In order to promote randomization in copolymerization and to control vinyl content, one or more modifiers may optionally be added to the polymerization ingredients. Amounts range from between 0 and about 90 or more equivalents per equivalent of lithium. Compounds useful as modifiers are typically organic and include those having an oxygen or nitrogen heteroatom and a non-bonded pair of electrons. Examples include dialkyl ethers of mono and oligo alkylene glycols; crown ethers; tertiary amines such as tetramethyethylene diamine (TMEDA); tetrahydrofuran (THF), THF oligomers linear and cyclic oligomeric oxolanyl alkanes and the like. Particular examples of these modifiers include potassium t-amylate and 2,2'-di(tetrahydrofuryl) propane. These modifiers are further described in U.S. Pat. No. 4,429,091, the disclosure of which in incorporated by reference.

Polymerization is begun by charging a blend of the monomer(s) and solvent to a suitable reaction vessel, followed by the addition of the modifier(s) and the initiator solution previously described. The procedure is carried out under anhydrous, anaerobic conditions. The reactants may be heated to a temperature of from about 23° C. to about 120° C., and are typically agitated for about 0.15 to about 24 hours.

After polymerization is complete, the product is removed from the heat and terminated with the functional reagents of the present invention as is conventionally done in the art, although termination could also be done without removal of heat. Prior to terminating the polymerization reaction with the functional end groups, a coupling agent may be added to the polymerization reaction to increase the Mooney viscosity to a desired range. Tin coupling agents such as tin tetrachloride ($SnCl_4$) are well known in the art and may be added in varying amounts, typically in amounts of 0 to about 0.9 mole equivalents functionality per each mole equivalent of anionic initiator depending upon the desired Mooney viscosity of the polymer.

The functional reagents reacted with the polymer are trialkyl or triarylsiloxy iminosilanes having the formula

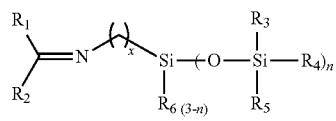

wherein $R_1$ to $R_6$ are $C_1$ to $C_{20}$ alkyl or aryl groups, optionally containing heteroatoms or functional groups, and x is equal to or greater than 1, and n is between 1 and 3. Typical heteroatoms may include N, O, and Si, and typical functional groups may include Cl, F, and Br. 3-(1-methylethylidene)aminopropyltris(trimethylsiloxy)silane is especially preferred as the iminosilane.

Optionally, upon termination, the functional terminated polymer could be quenched, if necessary, and dried. Quenching may be conducted by contacting the siloxane terminated polymer with a quenching agent for about 0.05 to about 2 hours at temperatures of from about 30° C. to about 120° C. to insure complete reaction. Suitable well known quenching agents include alcohols, water, carboxylic acids such 2-ethylhexanoic acid (EHA), acetic acid and the like. Alternative to, or in combination with, the step of quenching, the siloxy silane terminated polymer may be drum dried as is well known in the art. The use of steam or high heat to remove solvent is also well known in the art.

An antioxidant such as 2,6-di-t-butyl-4-methylphenol or butylated hydroxy toluene (BHT) may be added in solvent (hexane) solution, as is well known in the art. The antioxidant reduces the likelihood that Mooney viscosity instability is due to oxidative coupling.

The functionalizing agent is typically present in a molar ratio of about 0.25 to 2, and preferably about 0.5 to 1 based on moles of polymer.

While polymers produced with a final Mooney viscosity less than 150 are workable, less than 120 is preferred, and less than 100 more preferred. Ideally, 40 to 80 is the most preferred target range. Also, control of Mooney creep over time is one of the real advantages of the present invention. Under normal conditions, Mooney Unit (MU) growth of less than 40, preferably less than 20, and most preferably less than 10, over a storage period of up to two years is preferred.

The invention is further illustrated by reference to the following examples. It will be apparent to those skilled in the art that many modifications, both to the materials and methods, may be practiced without departing from the purpose and scope of the invention.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLES

Synthesis of 3-(1-methylethylidene)aminopropyltris (trimethylsiloxy)silane [MEAPTTSS]. A dry, nitrogen-purged 250 milliliter (mL) 3-neck round bottom flask was charged with 100 grams (g) (0.284 mol) 3-aminopropyltris (trimethylsiloxy)silane, 15.5 g $MgSO_4$ (0.128 mol), 100 g (150 mL) dry hexanes, and 23 mL (18.1 g, 0.313 mol, 1.10 equivalents) ACS (American Chemical Society) reagent grade acetone and stirred at room temperature under $N_2$ overnight (for approximately 18 hours). The milky suspension was filtered under nitrogen using a medium filter frit to remove the hydrated magnesium salts. The resulting clear, colorless solution was transferred to a capped bottle and the residual hexanes were removed by sparging with nitrogen. The product was a clear and colorless liquid. Yield 99 g, 89%. $^1H$ and $^{13}C$ NMR (nuclear magnetic resonance) analyses were performed to confirm product structure. $^{13}C$ NMR: 163, 55, 29, 24, 18, 0 ppm. $^1H$ NMR: 3.1 (t), 2.0 (s), 1.8 (s), 1.6 (m), 0.5 (m), 0.1 (s) ppm.

Sample 1: Synthesis of Trialkylsiloxyiminosilane Terminated Styrene-Butadiene Rubber (SBR)

A 100-gallon (379 liter) reactor was charged with the following: 52.7 kilograms (kg) dry hexanes, 82.4 kg of a 21.8 weight percent solution of 1,3-butadiene in hexanes (17.9 kg, 332.7 mol), and 29.8 kg of a 31.0 weight percent solution of styrene in hexanes (9.2 kg, 88.8 mol). The mixture was stirred and heated to 35° C. When the temperature target was reached, 0.48 kg of a 3 weight percent solution of n-BuLi in hexanes (14.4 g, 0.225 mol), 27 g of a 10 weight percent solution of 2,2'-isopropylidene bis (tetrahydrofuran) in hexanes (0.015 mol), and 15.2 g of a 15 weight percent solution of potassium t-amylate in hexanes (0.018 mol) were added. The reaction temperature reached a peak of 69.2° C. within 2 hours, at which time 44.9 g (0.11 mol, 0.50 equiv) of 3-(1-methylethylidene)aminopropyltris (trimethylsiloxy)silane (MEAPTTSS) was added. The reaction was stirred for 30 minutes, and the sample was removed from the reactor.

Comparative Samples 2 and 3: Synthesis of Alkoxysilane Terminated Styrene-Butadiene Rubber (SBR)

A 100-gallon (379 liter) reactor was charged with the following: 52.7 kilograms (kg) dry hexanes, 82.4 kg of a 21.8 weight percent solution of 1,3-butadiene in hexanes (17.9 kg, 332.7 mol), and 29.8 kg of a 31.0 weight percent solution of styrene in hexanes (9.2 kg, 88.8 mol). The mixture was stirred and heated to 35° C. When the temperature target was reached, 0.48 kg of a 3 weight percent solution of n-BuLi in hexanes (14.4 g, 0.225 mol), 27 g of a 10 weight percent solution of 2,2'-isopropylidene bis (tetrahydrofuran) in hexanes (0.015 mol), and 15.2 g of a 15 weight percent solution of potassium t-amylate in hexanes (0.018 mol) were added. The reaction temperature reached a peak of 69.2° C. within 2 hours, at which time 33.4 g (0.11 mol, 0.50 equiv) of 3-(1,3-dimethylbutylidene)aminopropyltriethoxysilane (DMBAPTS) was added. The reaction was stirred for 30 minutes, and half of the sample was removed from the reactor (sample 2) and the other half was moved to a blend tank (sample 3). In the blend tank, 218 g octyltriethoxysilane (OTES) (0.79 mol, 7 equivalents/Li) was added directly to the polymer cement and stirred at room temperature for 30 minutes. The excess OTES added was used as a Mooney viscosity stabilizing agent for the alkoxysilane functionalized rubber. The first portion of the polymer sample (sample 2) did not contain any stabilizing additives.

The three samples were dried via steam desolvatization and dried in an oven. Aging tests were performed in an ambient atmosphere oven at 70° C. over a period of 7 days. Mooney viscosity measurements were made before and after oven aging. Table 1 illustrates the impact of aging on the Mooney viscosity of the samples.

TABLE 1

| Sample # | 1 | 2 | 3 | 4 | 5 | 6 |
|---|---|---|---|---|---|---|
| DMBAPTS/Li Ratio | | 0.5 | 0.5 | | 0.9 | 0.9 |
| MEAPTTSS/Li Ratio | 0.5 | | | 0.9 | | |
| Stabilizer | | | OTES | | | OTES |
| Stabilizer/Li Ratio | 0.0 | 0.0 | 7.0 | 0.0 | 0.0 | 7.0 |
| Initial ML (1 + 4/100° C.) | 47.1 | 84.1 | 68.4 | 33.9 | 84.9 | 67.2 |
| ML after Aged 7 days @ 70° C. | 52.8 | 132.0 | 76.5 | 44.5 | 154.7 | 78.5 |
| Δ ML (1 + 4/100° C.) | +5.7 | +47.9 | +8.1 | +10.6 | +69.8 | +11.3 |

DMBAPTS = 3-(1,3-dimethylbutylidene)aminopropyltriethoxysilane
MEAPTTSS = 3-(1-methylethylidene)aminopropyltris(trimethylsiloxy)silane
OTES = octyltriethoxysilane As shown in Table 1, the preparation of living polymers synthesized via anionic polymerization, followed by reaction of the polymer with functionalizing agents such as trialkylsiloxy or triarylsiloxy iminosilanes (MEAPTTSS) demonstrate a significant improvement in controlling the Mooney growth of the polymer after aging. Polymers reacted with MEAPTTSS show superior Mooney viscosity stability growth than polymers terminated with DMBAPTS, even after addition of an excess of the stabilizing agent OTES and at different levels of functionalizing agent added. This demonstrates that polymers reacted with MEAPTTSS have inherently superior aging stability.

Comparative Sample 7: Synthesis of Silane Coupled, Non-Functionalized Styrene-Butadiene Rubber (SBR)

A 100-gallon (379 liter) reactor was charged with the following: 48.6 kilograms (kg) dry hexanes, 81.1 kg of a 21.8 weight percent solution of 1,3-butadiene in hexanes (17.7 kg, 315.5 mol), and 30.3 kg of a 31.4 weight percent solution of styrene in hexanes (9.5 kg, 91.7 mol). The mixture was stirred and heated to 35° C. When the temperature target was reached, 0.45 kg of a 3 weight percent solution of n-BuLi in hexanes (13.5 g, 0.211 mol), 32.6 g of a 10 weight percent solution of 2,2'-isopropylidene bis (tetrahydrofuran) in hexanes (0.018 mol), and 14.0 g of a 15 weight percent solution of potassium t-amylate in hexanes (0.017 mol) were added. The reaction temperature reached a peak of 70.9° C. within 1 hour, at which time 53 g (0.031 mol, 0.59 equiv Si—Cl/Li) of a 10 wt % solution of silicon tetrachloride ($SiCl_4$) in hexanes was added. The reaction was stirred for 30 minutes, moved to a blend tank, and dried using steam desolvatization. This polymer was utilized as a non-functional control for compounding comparison studies.

TABLE 2

Polymer Samples Mixed: properties and composition.

| | Sample # | | |
|---|---|---|---|
| | 7 | 8 | 9 |
| SBR Polymer Characteristics | | | |
| Wt. Percent Styrene | 38.7 | 36.7 | 37.3 |
| Percent 1,2- Vinyl Units | 31.3 | 27.5 | 25.3 |
| $ML_{(1+4/100° C.)}$ | 75.8 | 29.5 | 46.1 |
| Silane added (equiv./Li) | | | |
| MEAPTMSS | — | 0.50 | 0.50 |
| $SiCl_4$ | 0.15 | — | — |

TABLE 3

Mixing batch components

| Materials added | phr | grams |
|---|---|---|
| MASTERBATCH | | |
| Polymer (SBR, examples 7-9) | 80.0 | 121.3 |
| Natural rubber | 20.0 | 30.3 |
| Carbon black | 5.0 | 7.6 |
| Silica | 50.0 | 75.8 |
| Silane coupling agent | 5.0 | 7.6 |
| Black Oil | 10.0 | 15.2 |
| Stearic Acid | 2.0 | 3.0 |
| FINAL MIX | | |
| Masterbatch | 172.0 | 252.0 |
| Sulfur | 1.5 | 2.2 |
| TBBS | 2.5 | 3.7 |
| DPG | 1.4 | 2.1 |

TABLE 3-continued

Mixing batch components

| Materials added | phr | grams |
|---|---|---|
| 6PPD | 1.0 | 1.5 |
| Zinc Oxide | 2.5 | 3.7 |

Key:
Natural Rubber: NR20 grade, SIR20
Carbon Black: High structure N343, HAF
Silica: HISIL 190G precipitated silica, PPG
Silane coupling agent: EVONIC Si75, bis(triethoxysilylpropyl)polysulfide
Black Oil: Modified naphthenic oil, ERGON BO300
6PPD: SANTOFLEX 13 antioxidant (N-1,3-dimethylbutyl)-N'-phenyl-p-phenylenediamine
TBBS: SANTOCURE NS accelerator, N-tert-butyl-2-benzothiazolesulfenamide
DPG: Diphenylguanidine (accelerator)
phr—parts per hundred based on polymer Mixing Procedure (Masterbatch): Into a Brabender mixer, 75 wt. % of the HISIL 190G silica, N343 carbon black and stearic acid were added and mixed for 30 seconds with the SBR polymer. At this point, the black oil, Si75 coupling agent, and the remainder of the silica, black, and stearic acid were added into the mixer. The mixture was mixed until the internal temperature reached 170° C. or 6 minutes total time elapsed. The batch was then passed through a mill preheated to 40° C. with a ¼ inch gap four times, folding between passes, and removed. The batch was let rest for 1 hour before the remill step was performed.

Mixing Cycle (Remill): The Brabender mixer was preheated to 90° C., then charge with the masterbatch contents and mixed until temperature reaches 150° C. The material was removed from the mixer, and the batch was then passed through a mill preheated to 40° C. with a ¼ inch gap four times, folding between passes, and removed. The batch was let rest for 1 hour before the final mixing step was performed.

Mixing Cycle (Final): A Brabender mixer was preheated to 70° C., charged with the masterbatch rubber and the curing ingredients, and mixed until the temperature reaches 110° C. The material was removed from the mixer, and the batch was then passed through a mill preheated to 40° C. with a ¼ inch gap four times, folding between passes, and removed. The cured rubber batch material was then sheeted out and compounded for testing.

TABLE 4

Sample Compounding Analyses

| | | Example | | |
|---|---|---|---|---|
| | | 7 | 8 | 9 |
| Compound $ML_{(1+4/100° C.)}$ | | 85.2 | 64.8 | 81.0 |
| Tensile (MPa) | | 19.9 | 15.8 | 16.0 |
| 200% Modulus (MPa) | | 8.4 | 8.0 | 8.8 |
| 300% Modulus (MPa) | | 14.8 | 14.6 | 16.4 |
| Elongation (%) | | 374 | 316 | 304 |
| RDA Strain Sweep (5% Strain, 10 Hz) | | | | |
| 0° C. | G' | 6.55 | 4.82 | 4.50 |
| | G" | 3.19 | 1.99 | 1.82 |
| | Tan Δ | 0.486 | 0.414 | 0.403 |
| 65° C. | G' | 3.32 | 2.64 | 2.86 |
| 1st Strain | G" | 0.40 | 0.23 | 0.25 |
| | Tan Δ | 0.120 | 0.088 | 0.086 |
| | Delta G' | 2.040 | 0.413 | 0.743 |

Testing is done using ASTM standards techniques: Mooney viscosity: D-1646; Stress/strain: D-412.
Tan delta analyses was performed using a Rheometric Scientific RDAII, at 5% strain and 10 Hz.

The data in Table 4 show that the polymer reacted with the trialkylsiloxyiminosilane MEAPTTSS has superior hysteresis properties (Tan Δ) in rubber formulation than non-functionalized polymers, while retaining comparable physical properties (tensile strength, modulus, and elongation at break) without the accompanying Mooney growth issues observed with alkoxysilane terminated SBR polymers.

The stabilized polymers and methods of the present invention can be used separately with other equipment, methods and the like, to produce various elastomeric materials or compounds suitable for use in the production of various articles including pneumatic tires and the like, especially in the tread and sidewall portions of the tires. Thus, the scope of the invention shall include all modifications and variations that may fall within the scope of the attached claims. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of making a polymer comprising, polymerizing a conjugated diolefin in a hydrocarbon solvent in the presence of an initiator to form a living polymer, reacting the living polymer with a trialkylsiloxy or triarylsiloxy iminosilane functionalizing agent, and desolvatizing the polymer, resulting in a polymer with stable Mooney viscosity.

2. The method of claim 1, wherein the desolvatizing is performed by drum drying, direct drying, or steam desolvatizing.

3. The method of claim 1, wherein the iminosilane comprises

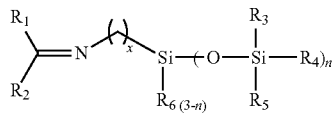

wherein R.sub.1 to R.sub.6 are C.sub.1 to C.sub.20 alkyl or aryl groups, optionally containing heteroatoms or functional groups, and x is equal to or greater than 1, and n is between 1 and 3.

4. The method of claim 1 wherein the iminosilane is 3-(1-methylethylidene)aminopropyltris(trimethylsiloxy)silane.

5. The method of claim 1, wherein the initiator is n-butyl lithium.

6. The method of claim 1, wherein the hydrocarbon solvent is one or more hexanes.

7. The method of claim 1, wherein the conjugated diolefin is 1,3-butadiene.

8. The method of claim 1, wherein the polymerizing step includes the presence of an aromatic vinyl compound.

9. The method of claim 8, wherein the aromatic vinyl compound is styrene.

10. The method of claim 1 including drying the polymer after steam desolvatizing.

11. The polymer produced by the process of claim 1.

12. A conjugated diolefin polymer containing trialkylsiloxy or triarylsiloxy iminosilane terminal end groups, having a stable Mooney viscosity.

13. A rubber composition containing a filler and the polymer of claim 12.

14. A tire comprising a sidewall and/or a tread containing the rubber of claim 13.

15. A method of making a polymer composition comprising adding a silica filler to the polymer made by the method of claim 1.

16. A method of making a polymer composition comprising adding a carbon black filler to the polymer made by the method of claim 1.

17. An iminosilane polymer functionalizing agent comprising

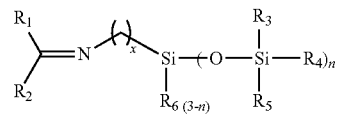

wherein R.sub.1 to R.sub.6 are C.sub.1 to C.sub.20 alkyl or aryl groups, optionally containing heteroatoms or functional groups, and x is equal to or greater than 1, and n is between 1 and 3.

18. The agent of claim 17 wherein the iminosilane is 3-(1-methylethylidene)aminopropyltris(trimethylsiloxy)silane.

* * * * *